United States Patent
Lyu et al.

(10) Patent No.: US 11,367,193 B2
(45) Date of Patent: Jun. 21, 2022

(54) SYSTEMS AND METHODS FOR MEDICAL IMAGING

(71) Applicant: UIH AMERICA, INC., Houston, TX (US)

(72) Inventors: Jingyuan Lyu, Houston, TX (US); Yu Ding, Houston, TX (US); Qi Liu, Houston, TX (US); Jian Xu, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 229 days.

(21) Appl. No.: 16/731,407

(22) Filed: Dec. 31, 2019

(65) Prior Publication Data

US 2021/0201490 A1  Jul. 1, 2021

(51) Int. Cl.
*G06T 7/00* (2017.01)
*G06T 7/136* (2017.01)
(Continued)

(52) U.S. Cl.
CPC ............ *G06T 7/0016* (2013.01); *A61B 5/055* (2013.01); *A61B 5/7285* (2013.01); *A61B 6/032* (2013.01); *A61B 6/037* (2013.01); *A61B 6/541* (2013.01); *G06K 9/6256* (2013.01); *G06T 7/136* (2017.01); *G06T 7/143* (2017.01); *G06V 10/267* (2022.01); *G06T 2207/20081* (2013.01); *G06T 2207/30048* (2013.01); *G06V 2201/031* (2022.01)

(58) Field of Classification Search
CPC ....... G06T 7/0016; G06T 7/136; G06T 7/143; G06T 2207/30048; G06T 2207/20081; G06K 9/342; G06K 9/6256; G06K 2209/051; A61B 5/7285; A61B 6/541; A61B 6/037; A61B 6/032; A61B 5/055
See application file for complete search history.

(56) References Cited

U.S. PATENT DOCUMENTS

| | | | |
|---|---|---|---|
| 6,434,412 B1 | 8/2002 | Simonetti et al. | |
| 9,655,522 B2 | 5/2017 | Li et al. | |

(Continued)

FOREIGN PATENT DOCUMENTS

CN    1106825 C    4/2003

OTHER PUBLICATIONS

Ahmad Shalbaf et al., "Automatic detection of end systole and end diastole within a sequence of 2-D echocardiographic images using modified Isomap algorithm", Apr. 19, 2011, 2011 1st Middle East Conference on Biomedical Engineering, p. 217-220. (Year: 2011).*

(Continued)

*Primary Examiner* — Brenda C Bernardi
(74) *Attorney, Agent, or Firm* — Metis IP LLC

(57) ABSTRACT

A method for medical imaging may include obtaining a plurality of successive images of a region of interest (ROI) including at least a portion of an object's heart. The plurality of successive images may be based on imaging data acquired from the ROI by a scanner without electrocardiography (ECG) gating. The plurality of successive images may be related to one or more cardiac cycles of the object's heart. The method may also include automatically determining, in the plurality of successive images, target images that correspond to at least one of the one or more cardiac cycles of the object's heart.

20 Claims, 8 Drawing Sheets

(51) Int. Cl.
  *G06T 7/143*   (2017.01)
  *G06K 9/62*    (2022.01)
  *A61B 5/00*    (2006.01)
  *A61B 6/00*    (2006.01)
  *A61B 6/03*    (2006.01)
  *A61B 5/055*   (2006.01)
  *G06V 10/26*   (2022.01)

(56) References Cited

U.S. PATENT DOCUMENTS

| | | | |
|---|---|---|---|
| 9,939,509 B2 | 4/2018 | Ahmad et al. | |
| 10,042,028 B2 | 8/2018 | Jo et al. | |
| 10,436,871 B2 | 10/2019 | Li et al. | |
| 10,672,151 B1 | 6/2020 | Ding et al. | |
| 2003/0161436 A1 | 8/2003 | Boyd et al. | |
| 2014/0133717 A1* | 5/2014 | Kabus | A61B 6/5288 382/128 |
| 2015/0374237 A1 | 12/2015 | Hu et al. | |
| 2019/0154785 A1* | 5/2019 | Zhou | G01R 33/56316 |
| 2021/0093277 A1* | 4/2021 | Jackson | A61B 6/5205 |

OTHER PUBLICATIONS

P. Kellman et al., Adaptive Sensitivity Encoding Incorporating Temporal Filtering (TSENSE), Magnetic Resonance in Medicine, 45: 846-852, 2001.

R. Ahmad et al., Variable Density incoherent Spatiotemporal Acquisition (VISTA) for Highly Accelerated Cardiac MRI, Magnetic Resonance in Medicine, 74(5): 1266-1278, 2015.

P. Kellman et al., Fully Automatic, Retrospective Enhancement of Real-time Acquired Cardiac Cine MR Images Using Image-Based Navigators and Respiratory Motion-Corrected Averaging, Magnetic Resonance in Medicine, 59: 771-778, 2008.

P. Kellman et al., High Spatial and Temporal Resolution Cardiac Cine MRI from Retrospective Reconstruction of Data Acquired in Real Time Using Motion Correction and Resorting, Magnetic Resonance in Medicine 62: 1557-1564, 2009.

Hui Xue et al., High Spatial and Temporal Resolution Retrospective Cine Cardiovascular Magnetic Resonance from Shortened Free Breathing Real-time Acquisitions, Journal of Cardiovascular Magnetic Resonance, 2013, 15 pages.

A. C. Larson et al., Self-Gated Cardiac Cine MRI, Magnetic Resonance in Medicine, 51: 93-102, 2004.

* cited by examiner

SYSTEMS AND METHODS FOR MEDICAL IMAGING

TECHNICAL FIELD

The present disclosure generally relates to medical imaging, and in particular, to systems and methods for determining target images that correspond to at least one cardiac cycle of an object's heart.

BACKGROUND

Cardiac cine images include a plurality of successive images of a region of interest (ROI) of a patient's heart that are acquired during a period of time when the heart relaxes and contracts repeatedly. The cardiac cine images are arranged in a temporal order and reflect the cardiac motion during the period of time. In the process of acquiring cardiac cine images, electrocardiograph (ECG) is usually used to monitor the cardiac motion and provide synchronization (gating) signal to an imaging system. Although ECG gating is considered the clinical standard for cardiac imaging, it is still problematic in several aspects. For example, firstly, cardiac imaging with ECG gating requires the patient to hold his/her breath for a long time. Secondly, the ECG signals could be unstable for some patients (e.g., patient with arrhythmia, hairy chest, or abnormal chest and cardiovascular geometry) and even difficult to obtain for some special applications (e.g., fetus cardiac scan). Cardiac imaging without ECG gating, however, cannot provide cardiac information such as which images correspond to the same cardiac cycle, or which images correspond to the start or end of cardiac diastole or cardiac systole, etc., while such information is important for a doctor to diagnose the heart's condition and disease. However, determining the cardiac information by analyzing the plurality of images with the naked eyes and experience of the doctor is not only time consuming but also often inaccurate. Therefore, it is desirable to provide methods and/or systems for automatic cardiac imaging to overcome the aforementioned problems.

SUMMARY

According to a first aspect of the present disclosure, a system for medical imaging may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a plurality of successive images of a region of interest (ROI) including at least a portion of an object's heart. The plurality of successive images may be based on imaging data acquired from the ROI by a scanner without electrocardiography (ECG) gating. The plurality of successive images may be related to one or more cardiac cycles of the object's heart. The one or more processors may automatically determine, in the plurality of successive images, target images that correspond to at least one of the one or more cardiac cycles of the object's heart.

In some embodiments, for at least one of the target images, the one or more processors may determine corresponding time information based on a temporal resolution of the plurality of successive images.

In some embodiments, to automatically determine, in the plurality of successive images, the target images that correspond to the at least one of the one or more cardiac cycles of the object's heart, the one or more processors may determine a reference image based on the plurality of successive images, the reference image relating to cardiac diastole of the object's heart. The one or more processors may determine correlations between the reference image and at least multiple of the plurality of successive images. The one or more processors may determine, in the plurality of successive images, diastolic images relating to the cardiac diastole based on the correlations. The one or more processors may determine two or more terminal images in the diastolic images. The one or more processors may determine the target images by including images between two neighboring terminal images of the two or more terminal images in the plurality of successive images.

In some embodiments, to determine the reference image based on the plurality of successive images, the one or more processors may divide the plurality of successive images into two or more first groups. The one or more processors may select one of the two or more first groups. A count of images in the selected first group may be greatest among the two or more first groups. The one or more processors may determine a median image based on the images of the selected first group. A pixel value of each pixel in the median image may be a median of pixel values of corresponding pixels of the images in the selected first group. The one or more processors may determine the reference image based on the median image.

In some embodiments, the plurality of successive images may be divided into the two or more first groups using K-means clustering.

In some embodiments, to determine the reference image based on the median image, the one or more processors may determine the median image as the reference image.

In some embodiments, to determine the reference image based on the median image, the one or more processors may determine a similarity degree between the median image and at least one of the images in the selected first group by comparing the pixel value of each pixel of the median image with the pixel value of the corresponding pixel in the at least one of the images in the selected first group. The one or more processors may determine one of the images in the selected first group as the reference image based on the similarity degree.

In some embodiments, to determine, in the plurality of successive images, the diastolic images relating to the cardiac diastole based on the correlations, the one or more processors may determine a median of the correlations of the at least multiple of the plurality of successive images. The one or more processors may determine the diastolic images based on the median of the correlations. The correlations of the diastolic images may be larger than the median of the correlations of the at least multiple of the plurality of successive images.

In some embodiments, to determine the two or more terminal images in the diastolic images, the one or more processors may divide the diastolic images into two or more second groups using K-means clustering. The one or more processors may determine a number for each of the diastolic images based on a time order of the diastolic images. In each of the two or more second groups, the one or more processors may determine the image the number of which is a median of the numbers of the diastolic images in the second group as the terminal image.

In some embodiments, to automatically determine, in the plurality of successive images, the target images that correspond to the at least one of the one or more cardiac cycles of the object's heart, the one or more processors may determine the target images using machine learning.

In some embodiments, to determine the target images using machine learning, the one or more processors may determine two or more terminal images in the plurality of successive images based on a first trained machine learning model. The one or more processors may determine the target images by including images between two neighboring terminal images of the two or more terminal images in the plurality of successive images.

In some embodiments, to determine the target images using machine learning, the one or more processors may determine diastolic images relating to cardiac diastole of the object's heart or systolic images relating to cardiac systole of the object's heart in the plurality of successive images using a second trained machine learning model. The one or more processors may determine two or more terminal images in the diastolic images or the systolic images. The one or more processors may determine the target images by including images between two neighboring terminal images of the two or more terminal images in the plurality of successive images.

In some embodiments, the plurality of successive images may be generated based on MR data using compressed sensing.

According to another aspect of the present disclosure, a method for medical imaging may include one or more of the following operations. One or more processors may obtain a plurality of successive images of a region of interest (ROI) including at least a portion of an object's heart. The plurality of successive images may be based on imaging data acquired from the ROI by a scanner without electrocardiography (ECG) gating. The plurality of successive images may be related to one or more cardiac cycles of the object's heart. The one or more processors may automatically determine, in the plurality of successive images, target images that correspond to at least one of the one or more cardiac cycles of the object's heart.

According to yet another aspect of the present disclosure, a system for medical imaging may include an image obtaining module configured to obtain a plurality of successive images of a region of interest (ROI) including at least a portion of an object's heart. The plurality of successive images may be based on imaging data acquired from the ROI by a scanner without electrocardiography (ECG) gating. The plurality of successive images may be related to one or more cardiac cycles of the object's heart. The system may also include an image selecting module configured to automatically determine, in the plurality of successive images, target images that correspond to at least one of the one or more cardiac cycles of the object's heart.

According to yet another aspect of the present disclosure, a non-transitory computer readable medium may comprise at least one set of instructions for medical imaging. The at least one set of instructions may be executed by one or more processors of a computing device. The one or more processors may obtain a plurality of successive images of a region of interest (ROI) including at least a portion of an object's heart. The plurality of successive images may be based on imaging data acquired from the ROI by a scanner without electrocardiography (ECG) gating. The plurality of successive images may be related to one or more cardiac cycles of the object's heart. The one or more processors may automatically determine, in the plurality of successive images, target images that correspond to at least one of the one or more cardiac cycles of the object's heart.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
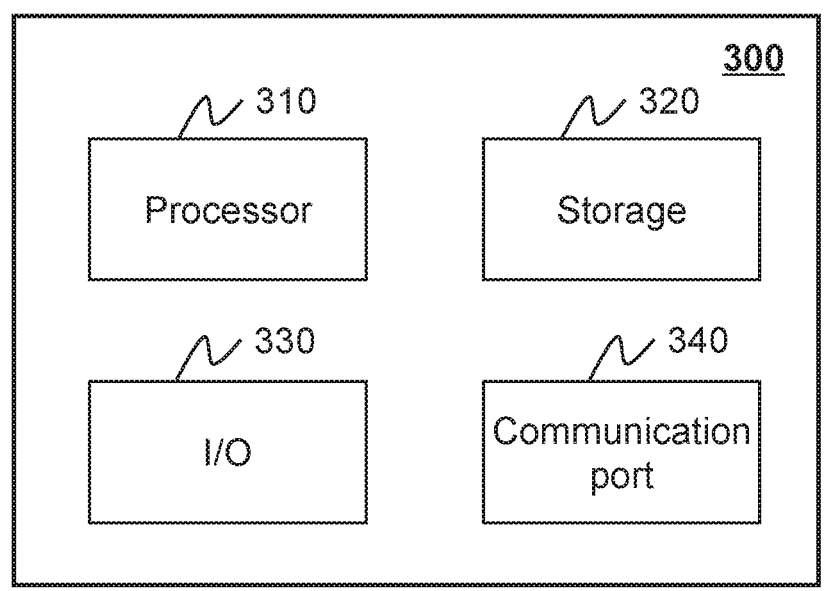
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system, a computed tomography (CT) system, a positron emission tomography (PET) system, or the like. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, a computed tomography-positron emission tomography (PET) system, etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

It should be noted that, in the present disclosure, an image, or a portion thereof (e.g., a region in the image) corresponding to an object (e.g., tissue, an organ, a tumor, etc.) may be referred to as an image, or a portion of thereof (e.g., a region) of or including the object, or the object itself. For instance, a region in an image that corresponds to or represents a heart may be described as that the region includes a heart. As another example, an image of or including a heart may be referred to a heart image, or simply heart. For brevity, that a portion of an image corresponding to or representing an object is processed (e.g., extracted, segmented, etc.) may be described as the object is processed. For instance, that a portion of an image corresponding to a heart is segmented from the rest of the image may be described as that the heart is segmented from the image.

A plurality of successive images, e.g., cardiac cine images, of a region of interest (ROI) of a patient's heart may be acquired without ECG gating. Cardiac imaging of the plurality of successive images without ECG gating, however, cannot provide cardiac information such as which images correspond to a same cardiac cycle, or which images correspond to the start or end of cardiac diastole or cardiac systole, etc., which is important for a doctor to diagnose the heart's condition and disease. An aspect of the present disclosure provides systems and methods for automatically determining the cardiac information of the plurality of successive images by analyzing the plurality of successive images (e.g., statistical analysis) and/or using machine learning.

Figure 1:
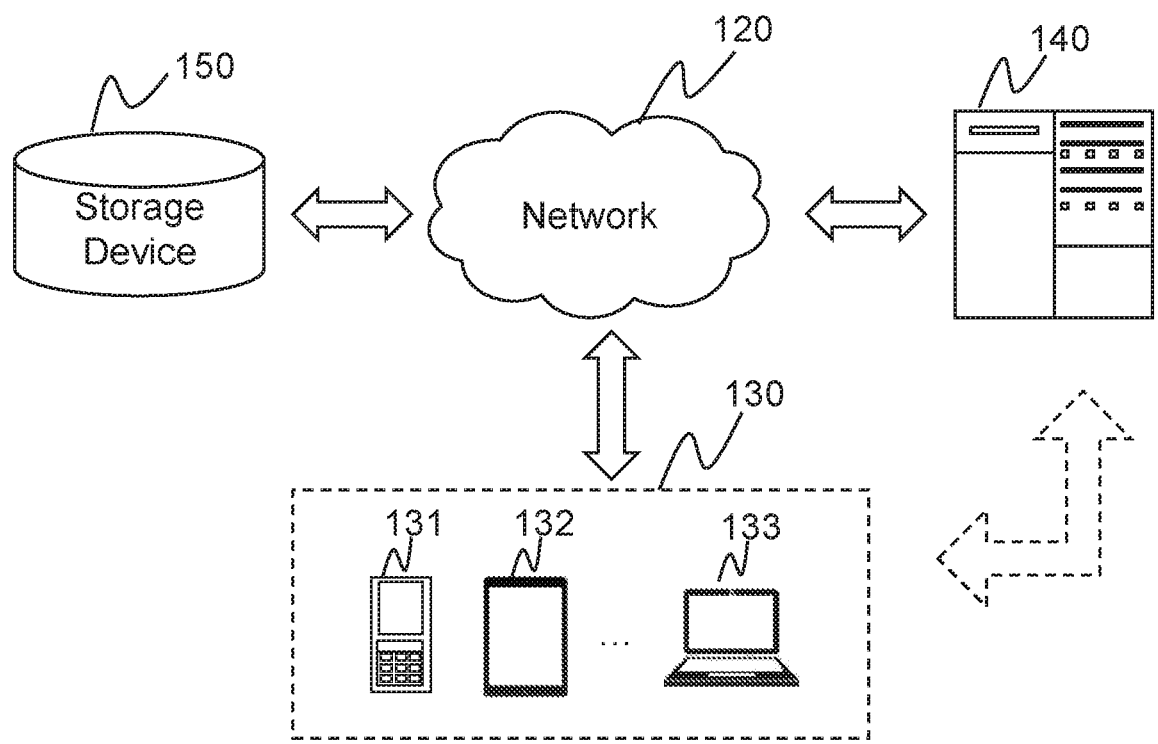
FIGS. 1 and 2 are a schematic diagram illustrating an exemplary image processing system according to some embodiments of the present disclosure.
Figure 2:
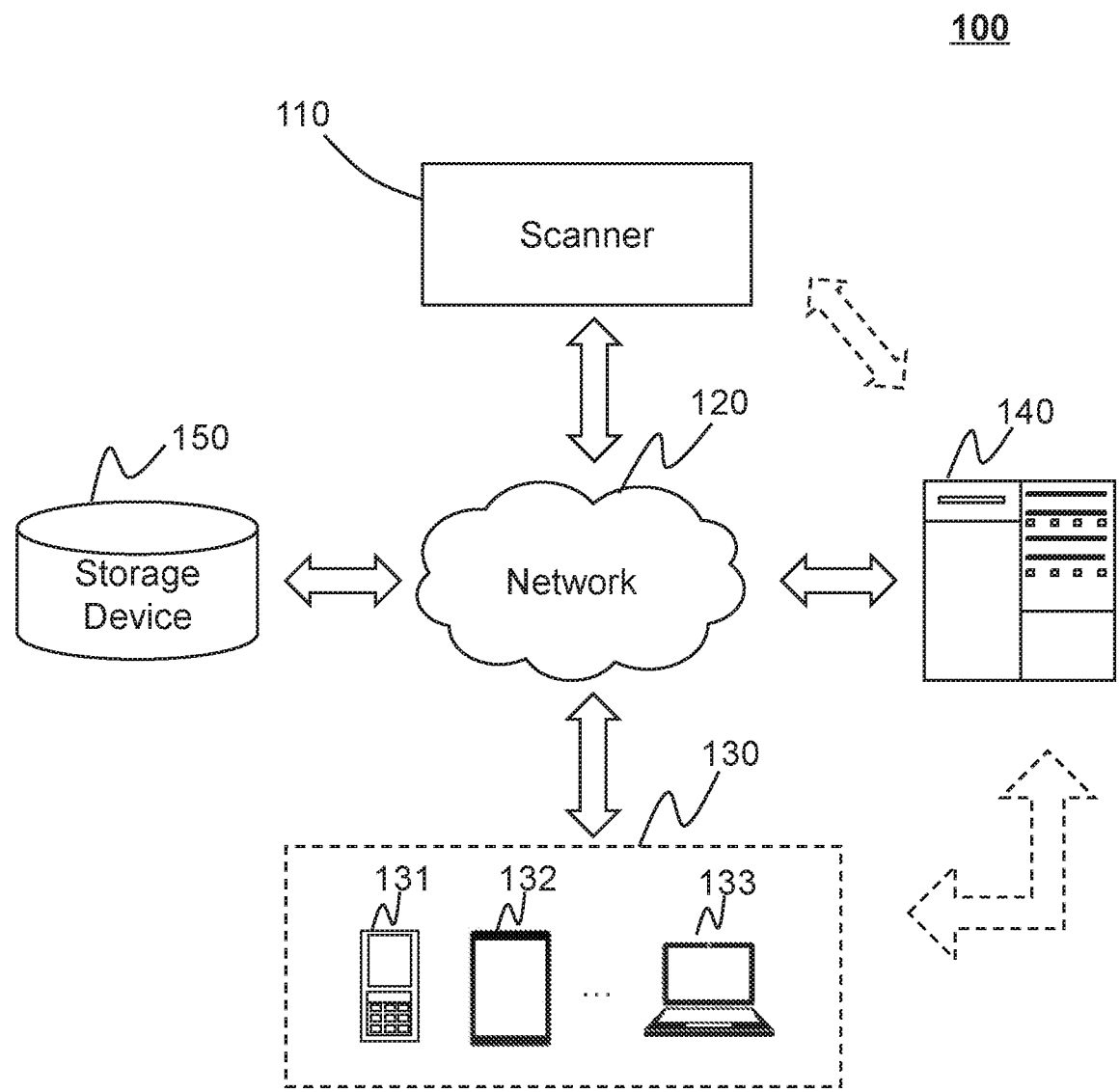

FIG. 1 is a schematic diagram illustrating an exemplary image processing system 100 according to some embodiments of the present disclosure. As illustrated, the image processing system 100 may include a network 120, a terminal 130, a processing device 140, and a storage device 150. Optionally, the image processing system 100 may further include a scanner 110 (e.g., as shown in FIG. 2).

The components of the image processing system 100 may be connected in one or more of various ways. Mere by way of example, as illustrated in FIG. 2, the scanner 110 may be connected to the processing device 140 through the network 120. As another example, the scanner 110 may be connected to the processing device 140 directly (as indicated by the bi-directional arrow in dotted lines linking the scanner 110 and the processing device 140). As a further example, as shown in FIGS. 1 and 2, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the terminal 130 and the processing device 140) or through the network 120.

The scanner 110 may scan an object located within its detection region and generate a plurality of data relating to the object (also referred to as imaging data). In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the scanner 110 may be an MRI scanner, a CT scanner, a PET scanner, or the like, or any combination thereof.

The network 120 may include any suitable network that can facilitate the exchange of information and/or data for the image processing system 100. In some embodiments, one or more components of the image processing system 100 (e.g., the scanner 110, the terminal 130, the processing device 140, or the storage device 150) may communicate information and/or data with one or more other components of the image processing system 100 via the network 120. For example, the processing device 140 may obtain imaging data from the scanner 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the image processing system 100 may be connected to the network 120 to exchange data and/or information.

The terminal 130 include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the terminal 130 may remotely operate the scanner 110 and/or the processing device 140. In some embodiments, the terminal 130 may operate the scanner 110 and/or the processing device 140 via a wireless connection. In some embodiments, the terminal 130 may receive information and/or instructions inputted by a user, and send the received information and/or instructions to the scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the scanner 110, the terminal 130, and/or the storage device 150. For example, the processing device 140 may obtain a plurality of successive images of a region of interest (ROI) of a patient's heart. The plurality of successive images may be generated based on imaging data that is acquired from the ROI without ECG gating. The processing device 140 may automatically determine, in the plurality of successive images, target images that correspond to at least one of cardiac cycle of the heart. In some embodiments, the processing device 140 may be a single server, or a server group. The server group may be centralized or distributed. In some embodiments, the processing device 140 may be local or remote. For example, the processing device 140 may access information and/or data stored in or acquired by the scanner 110, the terminal 130, and/or the storage device 150 via the network 120. As another example, the processing device 140 may be directly connected to the scanner 110 (as illustrated by the bidirectional arrow in dashed lines connecting the processing device 140 and the scanner 110 in FIG. 2), the terminal 130 (as illustrated by the bidirectional arrow in dashed lines connecting the processing device 140 and the terminal 130 in FIGS. 1 and 2), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the scanner 110, the terminal 130 and/or the processing device 140. For example, the storage device 150 may store one or more medical images. In some embodiments, the storage device 150 may store data and/or instructions that the processing device 140 may execute or use to perform exemplary methods described in the present disclosure. For example, the storage device 150 may store instructions that the processing device 140 may execute to automatically determine target images that correspond to at least one cardiac cycle. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the image processing system 100 (e.g., the scanner 110, the processing device 140, the terminal 130, etc.). One or more components of the image processing system 100 may access the data or instructions stored in the storage device 150 via the network 120. In some embodiments, the storage device 150 may be directly connected to or communicate with one or more components of the image processing system 100 (e.g., the scanner 110, the processing device 140, the terminal 130, etc.). In some embodiments, the storage device 150 may be part of the processing device 140.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may automatically determine target images that correspond to at least one cardiac cycle of an object's heart. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and step B may also be performed by two different processors jointly or separately in the computing device 300 (e.g., a first processor executes operation A and a second processor executes operation B, or the first and second processors jointly execute operations A and B).

The storage 320 may store data/information obtained from the scanner 110, the terminal 130, the storage device 150, or any other component of the image processing system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for determining target images that correspond to at least one cardiac cycle of an object's heart.

The I/O 330 may input or output signals, data, or information. In some embodiments, the I/O 330 may enable user interaction with the processing device 140. In some embodiments, the I/O 330 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof.

Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the scanner 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
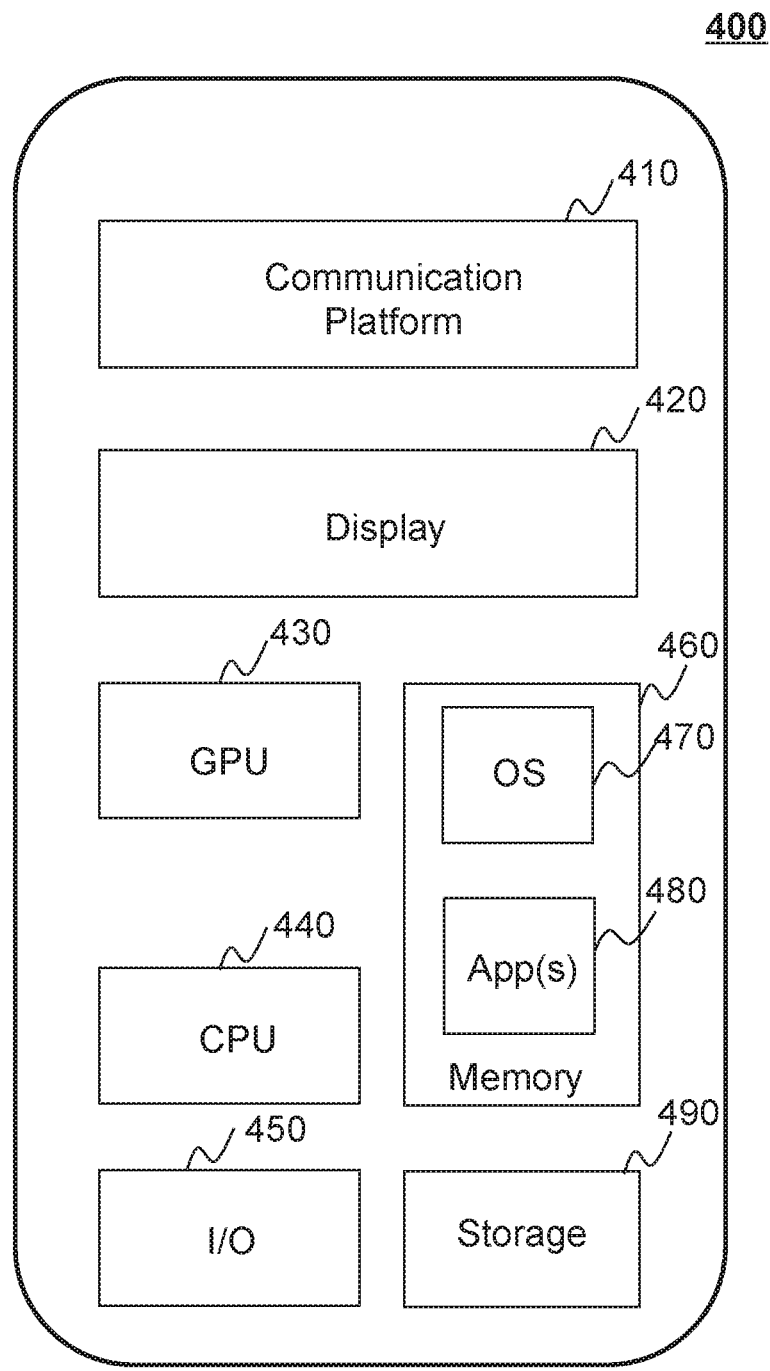
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the terminal 130 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the image processing system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
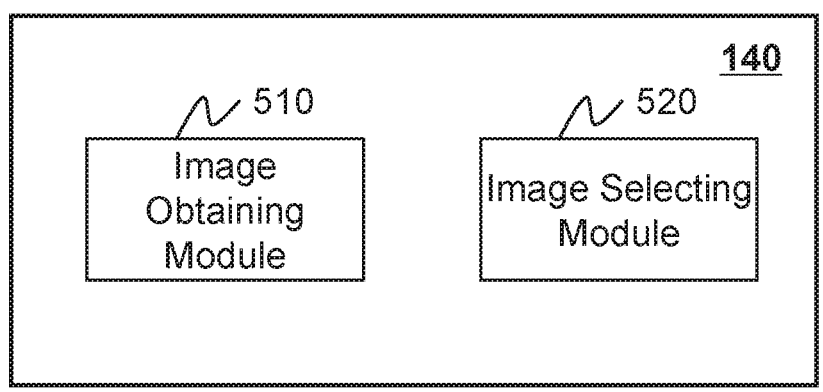
FIG. 5 is a schematic block diagram illustrating an exemplary processing device according to some embodiments of the present disclosure.

FIG. 5 is a schematic block diagram illustrating an exemplary processing device according to some embodiments of the present disclosure. The processing device 140 may include an image obtaining module 510 and an image selecting module 520.

The image obtaining module 510 may obtain a plurality of successive images of a region of interest (ROI) including at least a portion of an object's heart. In some embodiments, each of the plurality of successive images may present a state of the ROI of the object's heart at a certain time point. The plurality of successive images may be arranged in time order and may reflect the heartbeat of the object's heart during a period of time that include one or more cardiac cycles.

In some embodiments, the plurality of successive images may be based on imaging data acquired from the ROI by a medical scanner without electrocardiography (ECG) gating. The imaging data may be acquired using any suitable acquisition technology. The plurality of successive images may be generated using any suitable image reconstruction technology.

In some embodiments, the plurality of successive images may be MR images, CT images, PET images, or the like, or any combination thereof. In some embodiments, the plurality of successive images may be two-dimensional (2D) images or three-dimensional (3D) images.

The image selecting module 520 may automatically determine, in the plurality of successive images, target images that correspond to at least one of the one or more cardiac cycles of the object's heart.

Generally, the cardiac cycle of the heart includes a sequence of relaxations and contractions, resulting in events involving pumping blood from the heart and filling the heart with blood. In some embodiments, as used in the present disclosure, the cardiac cycle may refer to the performance (or activity) of the heart during an interval between any state of the heart and the next same or substantially similar state of the heart.

In some embodiments, during the cardiac cycle, the heart may undergo two events, cardiac diastole and cardiac systole. During the cardiac diastole, the heart relaxes and refill with blood, and during the cardiac systole, the heart contracts and pumps the blood out. With the repetition of cardiac cycles, the heart replenishes the blood with oxygen and drives blood throughout the body.

According to the description of the heart activity above, during the heart's periodic motion, the ventricles and the atria may relax and contract periodically and repetitively. In some embodiments, the activity of the heart (e.g., the cardiac diastole and the cardiac systole) may be represented by the activity of the ventricles or the atria. For example, the relaxation and the contraction of the ventricles may be referred to as ventricular diastole and ventricular systole and used to define a cardiac cycle. As another example, the relaxation and the contraction of the atria may be referred to as atrial diastole and atrial systole and used to define a cardiac cycle. The temporal corresponding relationship between the activities of the atria and the ventricles is generally known.

In some embodiments, the cardiac cycle may correspond to an interval between any state in the cardiac diastole (or the cardiac systole) and the same or substantially similar state in the next cardiac diastole (or the cardiac systole). For example, the cardiac cycle may correspond to an interval between the start of the cardiac diastole and the start of the next cardiac diastole. In this case, during the cardiac cycle, the cardiac diastole occurs first, then the cardiac systole. In other words, during the cardiac cycle, the heart (e.g., the ventricles or the atria) in a fully contracted state may relax and then contract to return to the fully contracted state. As another example, the cardiac cycle may correspond to an interval between the start of the cardiac systole and the start of the next cardiac systole. In this case, during the cardiac cycle, the cardiac systole occurs first, then the cardiac diastole. In other word, during the cardiac cycle, the heart (e.g., the ventricles or the atria) in a fully relaxed state may contract and then relax to return to the fully relaxed state.

In some embodiments, the start and/or the end of the cardiac cycle may be fixed. In some embodiments, the start and/or the end of the cardiac cycle may be defined by a user of the image processing system 100 (e.g., a doctor, a technician, or an engineer) or may be automatically determined by the image selecting module 520 based on, for example, the object's condition (e.g., the age, gender, health condition, etc.), the heart's disease, the goal of the imaging process, or the like, or any combination thereof. In some embodiments, the start and/or the end of the cardiac cycle may be defined by randomly selecting any state of the heart.

In some embodiments, the image selecting module 520 may determine, in the plurality of successive images, two or more terminal images each of which may corresponds to the start or end of a cardiac cycle. In some embodiments, each of the two or more terminal images may correspond to the same or substantially similar state of the heart, for example, the start or end of the cardiac diastole or the cardiac systole.

In some embodiments, the image selecting module 520 may determine the target images by including images, in the plurality of successive images, between two neighboring terminal images of the two or more terminal images. In some embodiments, the image selecting module 520 may further include at least one of the two or more terminal images into the target images. The target images may reflect the motion of the heart during at least one complete cardiac cycle.

In some embodiments, when the image selecting module 520 determines more than two terminal images, which indicates that the plurality of successive images may correspond to at least two complete cardiac cycles, an instruction of which set of the two neighboring terminal images are selected to determine the target images may be determined by the user or may be automatically determined by the image selecting module 520 based on, for example, the object's condition (e.g., the age, gender, health condition, etc.), the heart's disease, or the like, or any combination thereof. In some embodiments, the instruction may be determined in advance or during the process 600.

For example, the image selecting module 520 may determine three terminal images, image A, image B, and image C arranged in time order. In some embodiments, the image selecting module 520 may determine images between image A and image B as the target images. The image selecting module 520 may further determine image A and/or image B as the target image. In some embodiments, the image selecting module 520 may determine images between image B and image C as the target images. The image selecting module 520 may further determine image B and/or image C as the target image. In some embodiments, the image selecting module 520 may determine images between image A and image B and images between image B and image C as the target images. The image selecting module 520 may further determine at least one of image A, image B, and image C as the target image.

Figure 7:
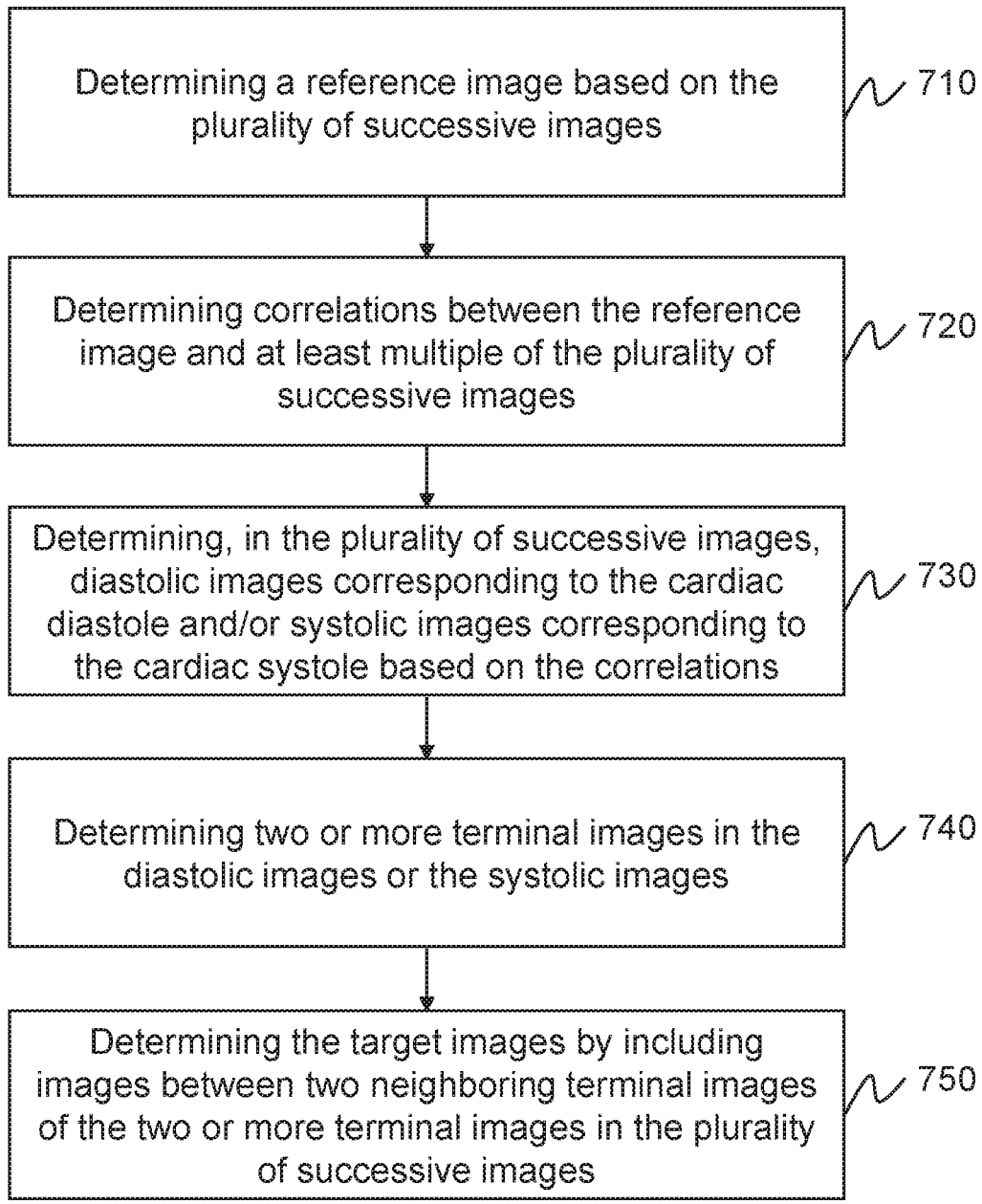
FIG. 7 is a flowchart illustrating an exemplary process for determining target images that correspond to at least one cardiac cycle of an object's heart according to some embodiments of the present disclosure.

An embodiment for determining the target images may be found elsewhere in the present disclosure (e.g., the description in connection with FIG. 7).

In some embodiments, the image selecting module 520 may determine the target images in the plurality of successive images using machine learning.

In some embodiments, the image selecting module 520 may determine, in the plurality of successive images, diastolic images that correspond to the cardiac diastole and systolic images that correspond to the cardiac systole using a first trained machine learning model. In some embodiments, the ROI of the object's heart presented in the diastolic image may be in the cardiac diastole. The ROI of the object's heart presented in the systolic image may be in the cardiac systole. The image selecting module 520 may determine two or more terminal images in the diastolic images and/or the systolic images based on the pre-defined start and/or end of the cardiac cycle. Alternatively, the image selecting module 520 may determine, in the diastolic images and/or the systolic images, two or more images that correspond to any same state of the heart as the terminal images. For example, the image selecting module 520 may determine the diastolic images each of which is immediately following a systolic image as the terminal images. In this case, the terminal images may be deemed as corresponding to the start of the cardiac diastole. As another example, the image selecting module 520 may determine the diastolic images each of which is immediately before a systolic image as the terminal images. In this case, the terminal images may be deemed as corresponding to the end of the cardiac diastole. As a further example, the image selecting module 520 may determine the systolic images each of which is immediately following a diastolic image as the terminal images. In this case, the terminal images may be deemed as corresponding to the start of the cardiac systole. As still a further example, the image selecting module 520 may determine the systolic images each of which is immediately before a diastolic image as the terminal images. In this case, the terminal images may be deemed as corresponding to the end of the cardiac systole. The image selecting module 520 may determine the target images by including images, in the plurality of successive images, between two neighboring terminal images of the two or more terminal images.

In some embodiments, the image selecting module 520 may determine two or more terminal images in the plurality of successive images using a second trained machine learning model. The image selecting module 520 may determine the target images by including images, in the plurality of successive images, between two neighboring terminal images of the two or more terminal images.

For example, according to the pre-defined start or end of the cardiac cycle, the second trained machine learning model may directly determine, in the plurality of successive images, two or more terminal images corresponding to the pre-defined start or end of the cardiac cycle. In some embodiments, the second trained machine learning model may have the ability of identifying images that correspond to one or more same or substantially similar states of the heart. For example, the second trained machine learning model may have the ability of identifying images that correspond to the start of the cardiac diastole and/or the ability of identifying images that correspond to the starts of the cardiac systole.

In some embodiments, the image selecting module 520 may determine the target images based on the first trained machine learning model and the second training machine learning model. For example, the image selecting module 520 may determine the diastolic images and the systolic images in the plurality of successive images using the first trained machine learning model. The image selecting module 520 may determine two or more terminal images in the diastolic images or the systolic images using the second trained machine learning model. The image selecting module 520 may determine the target images by including images, in the plurality of successive images, between two neighboring terminal images of the two or more terminal images.

In some embodiments, after determining the target images, the image selecting module 520 may determine a time stamp for each of the target images. For example, the image selecting module 520 may determine a time stamp, e.g., 0.5*TempRes (TempRes refers to the time resolution of the plurality of successive images), for the first image (e.g., the serial number is t) of the target images. From the second image (e.g., the serial number is t+1) of the target images, the image selecting module 520 may determine a time stamp for the target image by adding the time resolution of the plurality of successive images to the time stamp of the target image's previous image, e.g., 1.5*TempRes for the second image (e.g., the serial number is t+1) of the target images, 2.5*TempRes for the third images (e.g., the serial number is t+2) of the target images, . . . , and (0.5+n)*TempRes for the last images (e.g., the serial number is t+n) of the target images.

In some embodiments, the image selecting module 520 may mark at least one of the target images with the state of the heart that the target image corresponds to. For example, the image selecting module 520 may mark the target images that are deemed to correspond to the start of the cardiac diastole, the end of the cardiac diastole, the start of the cardiac systole, the end of the cardiac systole, the start of the ventricular systole, the end of the ventricular systole, the start of the ventricular diastole, the end of the ventricular diastole, the start of the atrial systole, the end of the atrial systole, the start of the atrial diastole, or the end of the atrial diastole.

In some embodiments, the image selecting module 520 may determine the interval corresponding to each of the at least one cardiac cycle.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of in the processing device 140. As another example, each of the components of the processing device 140 may include a storage device. Additionally or alternatively, the components of the processing device 140 may share a common storage device.

Figure 6:
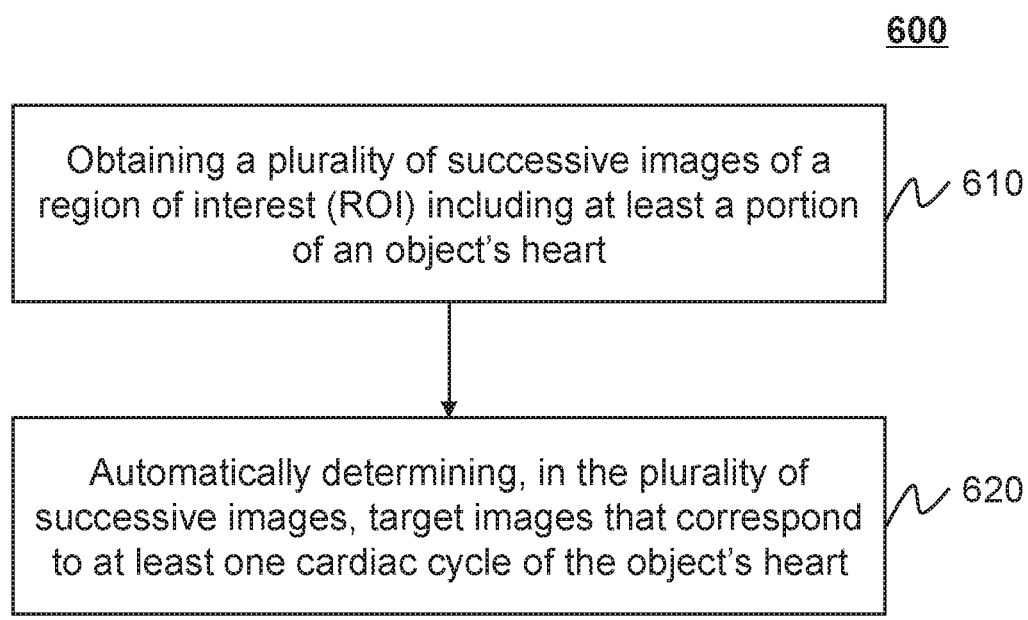
FIG. 6 is a flowchart illustrating an exemplary process for determining target images that correspond to at least one cardiac cycle of an object's heart according to some embodiments of the present disclosure.

FIG. 6 is a flowchart illustrating an exemplary process for determining target images that correspond to at least one cardiac cycle of an object's heart according to some embodiments of the present disclosure. In some embodiments, the process 600 may be implemented in the image processing system 100 illustrated in FIG. 1 or FIG. 2. For example, the process 600 may be stored in a storage medium (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 140 (e.g., the image obtaining module 510) may obtain a plurality of successive images of a region of interest (ROI) including at least a portion of an object's heart. In some embodiments, each of the plurality of successive images may present a state of the ROI of the object's heart at a certain time point. The plurality of successive images may be arranged in time order and may reflect the heartbeat of the object's heart during a period of time that include one or more cardiac cycles.

In some embodiments, the plurality of successive images may be based on imaging data acquired from the ROI by a medical scanner without electrocardiography (ECG) gating. The imaging data may be acquired using any suitable acquisition technology. The plurality of successive images may be generated using any suitable image reconstruction technology. Taking cardiac magnetic resonance imaging (CMRI) as an example, the description regarding MR data acquisition and/or image reconstruction in U.S. application Ser. No. 16/241,042 filed on Jan. 7, 2019 may be applied in the present disclosure to acquire the MR data and/or generate at least one of the plurality of successive images. The contents of U.S. application Ser. No. 16/241,042 are herein incorporated by reference in their entirety.

In some embodiments, the imaging data acquisition and the image reconstruction of the plurality of successive images may be performed by the image processing system 100 in FIG. 2. For example, the scanner 110 may acquire the imaging data from the ROI of the object's heart and transmit the imaging data to the processing device 140. The processing device 140 may generate the plurality of successive images based on the imaging data. In some embodiments, the imaging data acquisition and the image reconstruction of the plurality of successive images may be performed by other system. The processing device 140 may obtain the plurality of successive images from the other system.

In some embodiments, the plurality of successive images may be MR images, CT images, or the like, or any combination thereof. In some embodiments, the plurality of successive images may be two-dimensional (2D) images or three-dimensional (3D) images.

In 620, the processing device 140 (e.g., the image selecting module 520) may automatically determine, in the plurality of successive images, target images that correspond to at least one of the one or more cardiac cycles of the object's heart.

The heart may perform periodic motion to pump and fill blood. The heart is composed of four chambers: two atria on top and two ventricles on bottom. The atria receive blood from the body into the heart and the ventricles are responsible for pumping blood out of the heart. The right atrium takes in deoxygenated blood from the body through the superior and inferior vena cava. Since the right atrium and ventricle are relaxed and the atrioventricular valve between the two chambers is open, the blood flows into the right ventricle. An electrical impulse from the sinoatrial (SA) node tells the atrium to contract and push in the remaining blood and signals to the Purkinje fibers. The Purkinje fibers cause the ventricle to contract and pump the deoxygenated blood out of a semilunar valve into the pulmonary artery. The pulmonary artery takes the blood to the lungs, where it can be reoxygenated.

From the lungs, the oxygenated blood comes back into the heart via the pulmonary veins, and is received in the left atrium. The left atrium is relaxed and the atrioventricular valve is open. The blood passes though the valve into the left ventricle. The left ventricle then gets the message from the Purkinje fibers to contract. This contraction forces open the semilunar valve to the aorta, where the blood is pumped out to the rest of the body.

Because blood is circulating continuously, the heart doesn't have to wait for blood to return from the body or the lungs, so it is constantly filling up and pumping out. For this reason, the filling up of one side of the heart may be deemed as occurring at the same time as the filling up of other side, and the contraction of one side may be deemed as occurring simultaneously with the contraction of the other.

Generally, the cardiac cycle of the heart includes a sequence of relaxations and contractions, resulting in events involving pumping blood from the heart and filling the heart with blood. In some embodiments, as used in the present disclosure, the cardiac cycle may refer to the performance (or activity) of the heart during an interval between any state of the heart and the next same or substantially similar state of the heart. In some embodiments, while one particular state of the heart is captured by an image in a plurality of successive images, there might not be an image that corresponds to exactly the same particular state of the heart in the plurality of successive images. In the present disclosure, in some embodiments, when such "no exact same image exists" problem arises (and only when such problem arises), another image corresponding to a "substantially similar" state may be deemed acceptable to be used to define a cardiac cycle. Here, "substantially similar" refers to a state of the heart captured in an image, as compared to other states captured in other images, when the state is closest to the exact same state in the "start" of the cardiac cycle. In the systems and methods herein described, the image of the "same" state and the image of the "substantially similar" state can be used interchangeably.

In some embodiments, during the cardiac cycle, the heart may undergo two events, cardiac diastole and cardiac systole. During the cardiac diastole, the heart relaxes and refill with blood, and during the cardiac systole, the heart contracts and pumps the blood out. With the repetition of cardiac cycles, the heart replenishes the blood with oxygen and drives blood throughout the body.

According to the description of the heart activity above, during the heart's periodic motion, the ventricles and the atria may relax and contract periodically and repetitively. In some embodiments, the activity of the heart (e.g., the cardiac diastole and the cardiac systole) may be represented by the activity of the ventricles or the atria. For example, the relaxation and the contraction of the ventricles may be referred to as ventricular diastole and ventricular systole and used to define a cardiac cycle. As another example, the relaxation and the contraction of the atria may be referred to as atrial diastole and atrial systole and used to define a cardiac cycle. The temporal corresponding relationship between the activities of the atria and the ventricles is generally known.

In some embodiments, the cardiac cycle may correspond to an interval between any state in the cardiac diastole (or the cardiac systole) and the same or substantially similar state in the next cardiac diastole (or the cardiac systole). For example, the cardiac cycle may correspond to an interval between the start of the cardiac diastole and the start of the next cardiac diastole. In this case, during the cardiac cycle, the cardiac diastole occurs first, then the cardiac systole. In other words, during the cardiac cycle, the heart (e.g., the ventricles or the atria) in a fully contracted state may relax and then contract to return to the fully contracted state. As another example, the cardiac cycle may correspond to an interval between the start of the cardiac systole and the start of the next cardiac systole. In this case, during the cardiac cycle, the cardiac systole occurs first, then the cardiac diastole. In other word, during the cardiac cycle, the heart (e.g., the ventricles or the atria) in a fully relaxed state may contract and then relax to return to the fully relaxed state.

In some embodiments, the start and/or the end of the cardiac cycle may be fixed. In some embodiments, the start and/or the end of the cardiac cycle may be defined by a user of the image processing system 100 (e.g., a doctor, a technician, or an engineer) or may be automatically determined by the processing device 140 based on, for example, the object's condition (e.g., the age, gender, health condition, etc.), the heart's disease, the goal of the imaging process, or the like, or any combination thereof. In some embodiments, the start and/or the end of the cardiac cycle may be defined by randomly selecting any state of the heart. In some embodiments, the start and/or the end of the cardiac cycle may be defined in advance or during the process 600 (e.g., when the processing device 140 determines two or more terminal images).

In some embodiments, the processing device 140 may determine, in the plurality of successive images, two or more terminal images each of which may corresponds to the start or end of a cardiac cycle. In some embodiments, each of the two or more terminal images may correspond to the same or substantially similar state of the heart, for example, the start or end of the cardiac diastole or the cardiac systole.

In some embodiments, the processing device 140 may determine the target images by including images, in the plurality of successive images, between two neighboring terminal images of the two or more terminal images. In some embodiments, the processing device 140 may further include at least one of the two or more terminal images into the target images. The target images may reflect the motion of the heart during at least one complete cardiac cycle.

In some embodiments, when the processing device 140 determines more than two terminal images, which indicates that the plurality of successive images may correspond to at least two complete cardiac cycles, an instruction of which set of the two neighboring terminal images are selected to determine the target images may be determined by the user or may be automatically determined by the processing device 140 based on, for example, the object's condition (e.g., the age, gender, health condition, etc.), the heart's disease, or the like, or any combination thereof. In some embodiments, the instruction may be determined in advance or during the process 600.

For example, the processing device 140 may determine three terminal images, image A, image B, and image C arranged in time order. In some embodiments, the processing device 140 may determine images between image A and image B as the target images. The processing device 140 may further determine image A and/or image B as the target image. In some embodiments, the processing device 140 may determine images between image B and image C as the target images. The processing device 140 may further determine image B and/or image C as the target image. In some embodiments, the processing device 140 may determine images between image A and image B and images between image B and image C as the target images. The processing device 140 may further determine at least one of image A, image B, and image C as the target image.

An embodiment for determining the target images may be found elsewhere in the present disclosure (e.g., the description in connection with FIG. 7).

In some embodiments, the processing device 140 may determine the target images in the plurality of successive images using machine learning.

In some embodiments, the processing device 140 may determine, in the plurality of successive images, diastolic images that correspond to the cardiac diastole and systolic images that correspond to the cardiac systole using a first trained machine learning model. In some embodiments, the ROI of the object's heart presented in the diastolic image may be in the cardiac diastole. The ROI of the object's heart presented in the systolic image may be in the cardiac systole. The processing device 140 may determine two or more terminal images in the diastolic images and/or the systolic images based on the pre-defined start and/or end of the cardiac cycle. Alternatively, the processing device 140 may determine, in the diastolic images and/or the systolic images, two or more images that correspond to any same state of the heart as the terminal images. For example, the processing device 140 may determine the diastolic images each of which is immediately following a systolic image as the terminal images. In this case, the terminal images may be deemed as corresponding to the start of the cardiac diastole. As another example, the processing device 140 may determine the diastolic images each of which is immediately before a systolic image as the terminal images. In this case, the terminal images may be deemed as corresponding to the end of the cardiac diastole. As a further example, the processing device 140 may determine the systolic images each of which is immediately following a diastolic image as the terminal images. In this case, the terminal images may be deemed as corresponding to the start of the cardiac systole. As still a further example, the processing device 140 may determine the systolic images each of which is immediately before a diastolic image as the terminal images. In this case, the terminal images may be deemed as corresponding to the end of the cardiac systole. The processing device 140 may determine the target images by including images, in the plurality of successive images, between two neighboring terminal images of the two or more terminal images.

In some embodiments, the first trained machine learning model may be generated by training a first preliminary model using first sample data. The first sample data may include first sample images of different parts of the hearts of different patients. In some embodiments, the first sample images may include MR images, CT images, PET images, or the like, or any combination thereof. In some embodiments, the first sample images may be marked with diastolic images or systolic images.

In some embodiments, the processing device 140 may determine two or more terminal images in the plurality of successive images using a second trained machine learning model. The processing device 140 may determine the target images by including images, in the plurality of successive images, between two neighboring terminal images of the two or more terminal images.

For example, according to the pre-defined start or end of the cardiac cycle, the second trained machine learning model may directly determine, in the plurality of successive images, two or more terminal images corresponding to the pre-defined start or end of the cardiac cycle. In some embodiments, the second trained machine learning model may have the ability of identifying images that correspond to one or more same or substantially similar states of the heart. For example, the second trained machine learning model may have the ability of identifying images that correspond to the start of the cardiac diastole and/or the ability of identifying images that correspond to the starts of the cardiac systole.

In some embodiments, the second trained machine learning model may be generated by training a second preliminary model using second sample data. The second sample data may include second sample images of different parts of the hearts of different patients. In some embodiments, the second sample images may include MR images, CT images, PET images, or the like, or any combination thereof. In some embodiments, each of the second sample images may be marked with the state of the heart that the second sample image corresponds to.

In some embodiments, the processing device 140 may determine the target images based on the first trained machine learning model and the second training machine learning model. For example, the processing device 140 may determine the diastolic images and the systolic images in the plurality of successive images using the first trained machine learning model. The processing device 140 may determine two or more terminal images in the diastolic images or the systolic images using the second trained machine learning model. The processing device 140 may determine the target images by including images, in the plurality of successive images, between two neighboring terminal images of the two or more terminal images.

In some embodiments, the first trained machine learning model and/or the second trained machine learning model may include supervised learning, unsupervised learning, semi-supervised learning, reinforcement learning, or the like, or a combination thereof. In some embodiments, the first trained machine learning model and/or the second trained machine learning model may include a regression algorithm, a case learning algorithm, a formal learning algorithm, a decision tree learning algorithm, a Bayesian learning algorithm, a kernel learning algorithm, a clustering algorithm, an association rules learning algorithm, a neural network learning algorithm, a deep learning algorithm, a dimension reduction algorithm, etc. The regression algorithm may include a logistic regression algorithm, a stepwise regression algorithm, a multivariate adaptive regression splines algorithm, a locally estimated scatterplot smoothing algorithm, etc. The case learning algorithm may include a k-nearest neighbor algorithm, a learning vector quantization algorithm, a self-organizing map algorithm, etc. The formal learning algorithm may include a ridge regression algorithm, a least absolute shrinkage and selection operator (LAASSO) algorithm, an elastic net algorithm, etc. The decision tree learning algorithm may include a classification and regression tree algorithm, an iterative dichotomiser 3 (ID3) algorithm, a C4.5 algorithm, a chi-squared automatic interaction detection (CHAID) algorithm, a decision stump algorithm, a random forest algorithm, a mars algorithm, a gradient boosting machine (GBM) algorithm, etc. The Bayesian learning algorithm may include a naive Bayesian algorithm, an averaged one-dependence estimators algorithm, a Bayesian belief network (BBN) algorithm, etc. The kernel learning algorithm may include a support vector machine algorithm, a linear discriminate analysis algorithm, etc. The neural network learning algorithm may include a perceptron neural network algorithm, a back propagation algorithm, a Hopfield network algorithm, a self-organizing map (SOM) algorithm, a learning vector quantization algorithm, etc. The deep learning algorithm may include a restricted Boltzmann machine algorithm, a deep belief networks (DBN) algorithm, a convolutional neural network algorithm, a stacked auto-encoders algorithm, etc. The dimension reduction algorithm may include a principle component analysis algorithm, a partial least square regression algorithm, a Sammon mapping algorithm, a multi-dimensional scaling algorithm, a projection pursuit algorithm, etc.

In some embodiments, the first trained machine learning model and/or the second trained machine learning model may be generated by the image processing system 100 (e.g., the processing device 140) or other system.

In some embodiments, after determining the target images, the processing device 140 (e.g., the image selecting module 520) may determine a time stamp for each of the target images. For example, the processing device 140 may determine a time stamp, e.g., 0.5*TempRes (TempRes refers to the time resolution of the plurality of successive images), for the first image (e.g., the serial number is t) of the target images. From the second image (e.g., the serial number is t+1) of the target images, the processing device 140 may determine a time stamp for the target image by adding the time resolution of the plurality of successive images to the time stamp of the target image's previous image, e.g., 1.5*TempRes for the second image (e.g., the serial number is t+1) of the target images, 2.5*TempRes for the third images (e.g., the serial number is t+2) of the target images, . . . , and (0.5+n)*TempRes for the last images (e.g., the serial number is t+n) of the target images.

In some embodiments, the processing device 140 may mark at least one of the target images with the state of the heart that the target image corresponds to. For example, the processing device 140 may mark the target images that are deemed to correspond to the start of the cardiac diastole, the end of the cardiac diastole, the start of the cardiac systole, the end of the cardiac systole, the start of the ventricular systole, the end of the ventricular systole, the start of the ventricular diastole, the end of the ventricular diastole, the start of the atrial systole, the end of the atrial systole, the start of the atrial diastole, or the end of the atrial diastole.

In some embodiments, the processing device 140 may determine the interval corresponding to each of the at least one cardiac cycle.

In some embodiments, the processing device 140 may process the plurality of successive images to determine the target images by performing the process 600 immediately or substantially immediately after the plurality of successive images are generated, for example, at a defined time reasonably close to the time when the plurality of successive images are generated for an ordinary person in the art (e.g., 0.1 s, 1 s, 1 minute, 5 minutes, or 10 minutes, etc.). In some embodiments, the processing device 140 may process the plurality of successive images to determine the target images by performing the process 600 at a defined time reasonably long from the time when the plurality of successive images are generated for an ordinary person in the art (e.g., 20 minutes, 1 hour, or 1 day, etc.).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 7 is a flowchart illustrating an exemplary process for determining target images that correspond to at least one cardiac cycle of an object's heart according to some embodiments of the present disclosure. In some embodiments, the process 700 may be implemented in the image processing system 100 illustrated in FIG. 1 or FIG. 2. For example, the process 700 may be stored in a storage medium (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, the processing device 140 may perform operation 620 of the process 600 in FIG. 6 based on the process 700.

In 710, the processing device 140 (e.g., the image selection module 520) may determine a reference image based on the plurality of successive images. In some embodiments, the reference image may be used to determine diastolic images or systolic images in the plurality of successive images. In some embodiments, the reference image may be a diastolic image or a systolic image. For example, if the reference image is a diastolic image, the reference image may be used to determine the diastolic images in the plurality of successive images. As another example, if the reference image is a systolic image, the reference image may be used to determine the systolic images in the plurality of successive images.

Since in a cardiac cycle, the count of diastolic images may be greater than the count of systolic images, there may be more diastolic images than the systolic images in the plurality of successive images. According to the plurality of successive images, the result for determining a diastolic image may be more accurate than the result for determining a systolic image. Therefore, preferably, the processing device 140 may choose an image corresponding to the cardiac diastole as a reference image from the plurality of successive images.

In some embodiments, the processing device 140 may determine the reference image corresponding to the cardiac diastole by performing the following operations.

The processing device 140 may divide the plurality of successive images into two or more first groups based on the similarity of pixel values of pixels in the plurality of successive images. In some embodiments, the processing device 140 may divide the plurality of successive images into the two or more first groups using K-means clustering.

Since in a cardiac cycle, the count of diastolic images may be greater than the count of systolic images, there may be more diastolic images than the systolic images in the plurality of successive images. The first group in which a count of images is greatest among the two or more first groups is the most likely one to only include the diastolic images. So, the processing device 140 may select one of the two or more first groups in which a count of images is greatest among the two or more first groups.

The processing device 140 may determine a median image based on the images of the selected first group. A pixel value of each pixel in the median image may be a median of pixel values of corresponding pixels of the images in the selected first group.

The processing device 140 may determine the reference image based on the median image. The determined reference image may be deemed as corresponding to the cardiac diastole.

For example, the processing device 140 may determine the median image as the reference image. As another example, the processing device 140 may determine an image in the selected first group as the reference image based on the median image. Merely by way of example, the processing device 140 may determine a similarity degree between the median image and at least one of the images in the selected first group by comparing the pixel value of each pixel of the median image with the pixel value of the corresponding pixel in the at least one of the images in the selected first group. For example, the processing device 140 may determine a difference between the pixel value of each pixel of the median image and the pixel value of the corresponding pixel in the at least one of the images in the selected first group. The processing device 140 may determine the similarity degree by determining an average of the differences, a sum of the differences, an average of the squares of the differences, or a sum of the squares of the differences.

The processing device 140 may determine one of the images in the selected first group as the reference image based on the similarity degree. For example, the processing device 140 may determine the image corresponding to which the similarity degree is smallest as the reference image. Alternatively or additionally, the processing device 140 may determine the image corresponding to which the similarity degree is less than a similarity threshold as the reference image.

In 720, the processing device 140 (e.g., the image selecting module 520) may determine correlations between the reference image and at least multiple of the plurality of successive images. Preferably, the processing device 140 may determine a correlation between the reference image and each of the plurality of successive images.

Merely by way of example, the processing device 140 may determine the correlation between the reference image and each of the plurality of successive images based on Equation (1) below:

$$C(t) = -\frac{1}{2}\|I0 - I(t)\|_2^2, \quad (1)$$

wherein I0 refers to the reference image; I(t) refers to one of the plurality of successive images; and C(t) refers to the correlation between the reference image and the one of the plurality of successive images.

In 730, the processing device 140 (e.g., the image selecting module 520) may determine, in the plurality of successive images, diastolic images corresponding to the cardiac diastole of the object's heart and/or systolic images corresponding to the cardiac systole of the object's heart based on the correlations.

In some embodiments, the processing device 140 may determine a median of the correlations. The processing device 140 may determine, in the plurality of successive images, the diastolic images and/or the systolic images based on the median of the correlations. For example, the reference image may be a diastolic image. The processing device 140 may determine, in the plurality of successive images, the images corresponding to which the correlations are larger than the median of the correlations as the diastolic images. As another example, the reference image may be a systolic image. The processing device 140 may determine, in the plurality of successive images, the images corresponding to which the correlations are larger than the median of the correlations as the systolic images.

Figure 8:
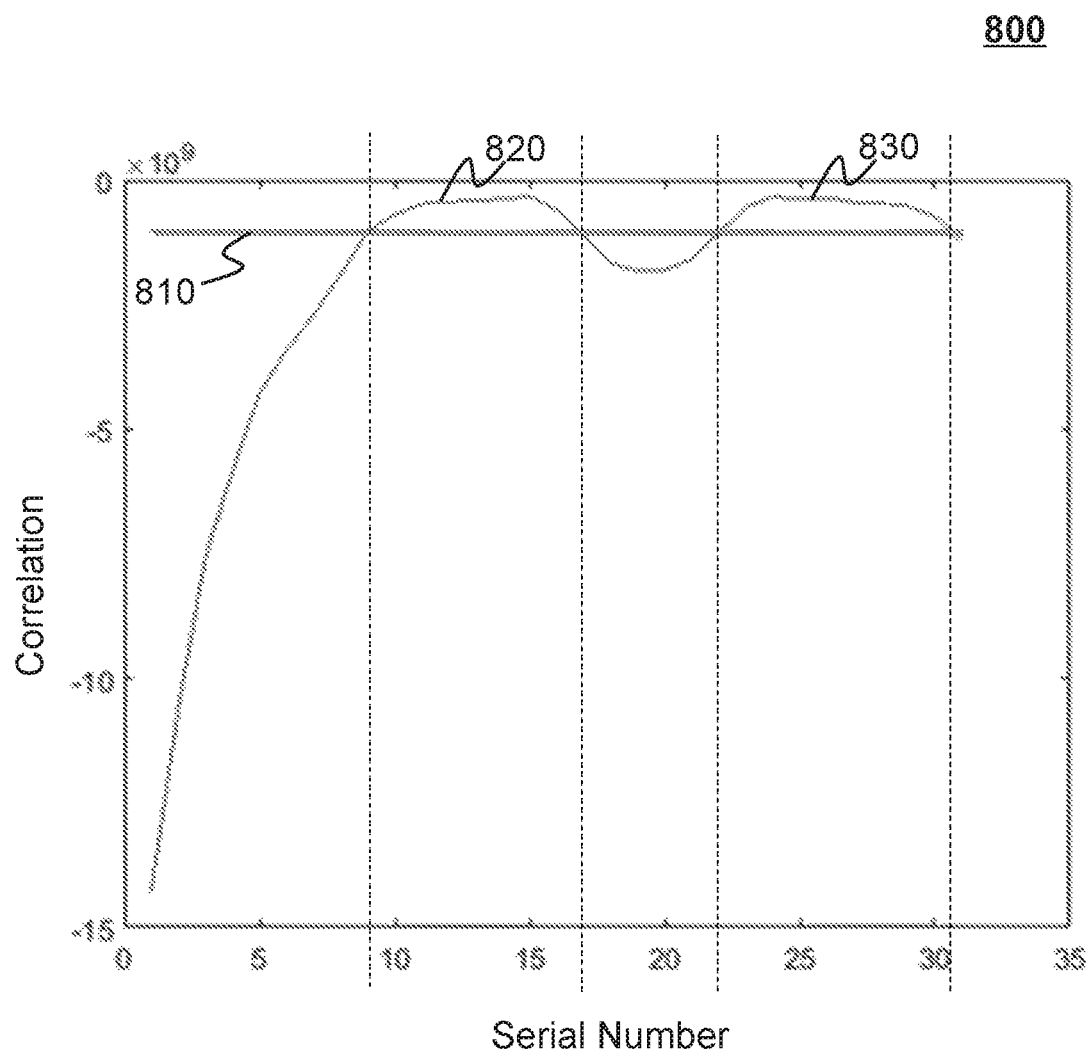
FIG. 8 is a schematic diagram illustrating an exemplary correlation curve generated based on a correlation between a reference image and each of a plurality of successive images according to some embodiments of the present disclosure.

Merely by way of example, FIG. 8 is a schematic diagram illustrating an exemplary correlation curve generated based on the correlation between the reference image corresponding to the cardiac diastolic and each of the plurality of successive images according to some embodiments of the present disclosure. In the embodiment of FIG. 8, the reference image may be an image corresponding to the cardiac diastole.

In some embodiments, the processing device 140 may determine a serial number for each of the plurality of successive images based on the time order of the plurality of successive images, for example, 1-40 for the 40 successive images, respectively. The correlation curve 800 may indicate a relation between the correlation and the serial number of the image corresponding to the correlation. As shown in FIG. 8, the horizontal axis of the correlation curve 800 indicates the serial numbers of the plurality of successive images. The vertical axis of the correlation curve 800 indicates the correlation between the reference image and each of the plurality of successive images.

As shown in FIG. 8, line 810 indicates the median of the correlations. The images corresponding to the portion 820 and the portion 830 of the correlation curve 800, corresponding to which the correlations are larger than the median of the correlations, may be determined as the diastolic images.

In 740, the processing device 140 (e.g., the image selection module 520) may determine two or more terminal images in the diastolic images or the systolic images.

Merely by way of example, the processing device 140 may determine a serial number for each of the plurality of successive images based on the time order of the plurality of successive images, for example, 1-40 for the 40 successive images, respectively. The processing device 140 may determine the diastolic images in the plurality of successive images based on the reference image corresponding to the cardiac diastole. The processing device 140 may divide the determined diastolic images into two or more second groups based on the similarity of pixel values of pixels in the determined diastolic images and/or the serial numbers of the determined diastolic images. In some embodiments, the processing device 140 may divide the determined diastolic images into the two or more second groups using K-means clustering. In some embodiments, the images in the second group may be deemed as reflecting the cardiac diastole. For at least two of the two or more second groups, the processing device 140 may determine the images at the same location (e.g., the first location, the last location, or the middle location, etc.) in the at least two of the two or more second groups as the two or more terminal images. For example, for at least two of the two or more second groups, the processing device 140 may determine a median of the serial numbers of the images in the second group. The image of which the serial number is equal to the median of the serial numbers may be determined as the terminal image.

In some embodiments, the processing device 140 may determine the two or more terminal images in the diastolic images or the systolic images using machine learning, e.g., the second trained machine learning model described above in the operation 620 of the process 600 in FIG. 6.

In 750, the processing device 140 (e.g., the image selection module 520) may determine the target images by including images between two neighboring terminal images of the two or more terminal images in the plurality of successive images.

For example, the processing device 140 may determine two terminal images, image j and image j+h. The processing device 140 may determine the target images by including images j+1 to j+h−1 in the plurality of successive images. In some embodiments, the processing device 140 may further include image j and/or image j+h in the target images.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for medical imaging, comprising:
   at least one storage device including a set of instructions; and
   at least one processor in communication with the at least one storage device, wherein when executing the set of instructions, the at least one processor is directed to cause the system to:

obtain a plurality of successive images of a region of interest (ROI) including at least a portion of an object's heart, wherein:
the plurality of successive images are based on imaging data acquired from the ROI by a scanner without electrocardiography (ECG) gating, and
the plurality of successive images are related to one or more cardiac cycles of the object's heart;
automatically determine, in the plurality of successive images, target images that correspond to at least one of the one or more cardiac cycles of the object's heart; and
for at least one of the target images, determine corresponding time information based on a temporal resolution of the plurality of successive images.

2. The system of claim 1, wherein to automatically determine, in the plurality of successive images, the target images that correspond to the at least one of the one or more cardiac cycles of the object's heart, the at least one processor is further directed to cause the system to:
determine a reference image based on the plurality of successive images, the reference image relating to cardiac diastole of the object's heart;
determine correlations between the reference image and at least multiple of the plurality of successive images;
determine, in the plurality of successive images, diastolic images relating to the cardiac diastole based on the correlations;
determine two or more terminal images in the diastolic images; and
determine the target images by including images between two neighboring terminal images of the two or more terminal images in the plurality of successive images.

3. The system of claim 2, wherein to determine the reference image based on the plurality of successive images, the at least one processor is further directed to cause the system to:
divide the plurality of successive images into two or more first groups;
select one of the two or more first groups, a count of images in the selected first group being greatest among the two or more first groups;
determine a median image based on the images of the selected first group, a pixel value of each pixel in the median image being a median of pixel values of corresponding pixels of the images in the selected first group; and
determine the reference image based on the median image.

4. The system of claim 3, wherein to determine the reference image based on the median image, the at least one processor is further directed to cause the system to:
determine the median image as the reference image; or
wherein to determine the reference image based on the median image, the at least one processor is further directed to cause the system to:
determine a similarity degree between the median image and at least one of the images in the selected first group by comparing the pixel value of each pixel of the median image with the pixel value of the corresponding pixel in the at least one of the images in the selected first group; and
determine one of the images in the selected first group as the reference image based on the similarity degree.

5. The system of claim 2, wherein to determine, in the plurality of successive images, the diastolic images relating to the cardiac diastole based on the correlations, the at least one processor is further directed to cause the system to:
determine a median of the correlations of the at least multiple of the plurality of successive images; and
determine the diastolic images based on the median of the correlations, the correlations of the diastolic images being larger than the median of the correlations of the at least multiple of the plurality of successive images.

6. The system of claim 2, wherein to determine the two or more terminal images in the diastolic images, the at least one processor is further directed to cause the system to:
divide the diastolic images into two or more second groups using K-means clustering;
determine a number for each of the diastolic images based on a time order of the diastolic images; and
in each of the two or more second groups, determine the image the number of which is a median of the numbers of the diastolic images in the second group as the terminal image.

7. The system of claim 1, wherein to automatically determine, in the plurality of successive images, the target images that correspond to the at least one of the one or more cardiac cycles of the object's heart, the at least one processor is further directed to cause the system to:
determine the target images using machine learning.

8. The system of claim 7, wherein to determine the target images using machine learning, the at least one processor is further directed to cause the system to:
determine two or more terminal images in the plurality of successive images based on a first trained machine learning model; and
determine the target images by including images between two neighboring terminal images of the two or more terminal images in the plurality of successive images.

9. The system of claim 7, wherein to determine the target images using machine learning, the at least one processor is further directed to cause the system to:
determine diastolic images relating to cardiac diastole of the object's heart or systolic images relating to cardiac systole of the object's heart in the plurality of successive images using a second trained machine learning model;
determine two or more terminal images in the diastolic images or the systolic images; and
determine the target images by including images between two neighboring terminal images of the two or more terminal images in the plurality of successive images.

10. The system of claim 1, wherein the plurality of successive images are generated based on MR data using compressed sensing.

11. A method for medical imaging implemented on a machine having one or more processors and one or more storage devices, the method comprising:
obtaining a plurality of successive images of a region of interest (ROI) including at least a portion of an object's heart, wherein:
the plurality of successive images are based on imaging data acquired from the ROI by a scanner without electrocardiography (ECG) gating, and
the plurality of successive images are related to one or more cardiac cycles of the object's heart;
automatically determining, in the plurality of successive images, target images that correspond to at least one of the one or more cardiac cycles of the object's heart; and
for at least one of the target images, determining corresponding time information based on a temporal resolution of the plurality of successive images.

12. The method of claim 11, wherein the automatically determining, in the plurality of successive images, the target images that correspond to the at least one of the one or more cardiac cycles of the object's heart includes:
- determining a reference image based on the plurality of successive images, the reference image relating to cardiac diastole of the object's heart;
- determining correlations between the reference image and at least multiple of the plurality of successive images;
- determining, in the plurality of successive images, diastolic images relating to the cardiac diastole based on the correlations;
- determining two or more terminal images in the diastolic images; and
- determining the target images by including images between two neighboring terminal images of the two or more terminal images in the plurality of successive images.

13. The method of claim 12, wherein the determining the reference image based on the plurality of successive images includes:
- dividing the plurality of successive images into two or more first groups;
- selecting one of the two or more first groups, a count of images in the selected first group being greatest among the two or more first groups;
- determining a median image based on the images of the selected first group, a pixel value of each pixel in the median image being a median of pixel values of corresponding pixels of the images in the selected first group; and
- determining the reference image based on the median image.

14. The method of claim 13, wherein the determining the reference image based on the median image includes:
- determining the median image as the reference image; or
- wherein the determining the reference image based on the median image includes:
  - determining a similarity degree between the median image and at least one of the images in the selected first group by comparing the pixel value of each pixel of the median image with the pixel value of the corresponding pixel in the at least one of the images in the selected first group; and
  - determining one of the images in the selected first group as the reference image based on the similarity degree.

15. The method of claim 12, wherein the determining, in the plurality of successive images, the diastolic images relating to the cardiac diastole based on the correlations includes:
- determining a median of the correlations of the at least multiple of the plurality of successive images; and
- determining the diastolic images based on the median of the correlations, the correlations of the diastolic images being larger than the median of the correlations of the at least multiple of the plurality of successive images.

16. The method of claim 12, wherein the determining the two or more terminal images in the diastolic images includes:
- dividing the diastolic images into two or more second groups using K-means clustering;
- determining a number for each of the diastolic images based on a time order of the diastolic images; and
- in each of the two or more second groups, determining the image the number of which is a median of the numbers of the diastolic images in the second group as the terminal image.

17. The method of claim 11, wherein the automatically determining, in the plurality of successive images, the target images that correspond to the at least one of the one or more cardiac cycles of the object's heart includes:
- determining the target images using machine learning.

18. The method of claim 17, wherein the determining the target images using machine learning includes:
- determining two or more terminal images in the plurality of successive images based on a first trained machine learning model; and
- determining the target images by including images between two neighboring terminal images of the two or more terminal images in the plurality of successive images; or
- wherein the determining the target images using machine learning includes:
  - determining diastolic images relating to cardiac diastole of the object's heart or systolic images relating to cardiac systole of the object's heart in the plurality of successive images using a second trained machine learning model;
  - determining two or more terminal images in the diastolic images or the systolic images; and
  - determining the target images by including images between two neighboring terminal images of the two or more terminal images in the plurality of successive images.

19. The method of claim 11, wherein the plurality of successive images are generated based on MR data using compressed sensing.

20. A non-transitory computer readable medium, comprising at least one set of instructions for medical imaging, wherein when executed by one or more processors of a computing device, the at least one set of instructions directs the one or more processors to perform a method, the method comprising:
- obtaining a plurality of successive images of a region of interest (ROI) including at least a portion of an object's heart, wherein:
  - the plurality of successive images are based on imaging data acquired from the ROI by a scanner without electrocardiography (ECG) gating, and
  - the plurality of successive images are related to one or more cardiac cycles of the object's heart; and
- automatically determining, in the plurality of successive images, target images that correspond to at least one of the one or more cardiac cycles of the object's heart; and
- for at least one of the target images, determining corresponding time information based on a temporal resolution of the plurality of successive images.

* * * * *